US008273367B2

(12) United States Patent
Pesce et al.

(10) Patent No.: US 8,273,367 B2
(45) Date of Patent: Sep. 25, 2012

(54) ARTICLES COMPRISING A MINT ODOR-FREE COOLING AGENT

(75) Inventors: Antonella Pesce, Pescara (IT); Daniela Meo, Salerno (IT); Giovanni Carlucci, Chieti (IT); Achille Di Cintio, Pescara (IT)

(73) Assignee: The Procter and Gamble Company, Cincinnati, OH (US)

( * ) Notice: Subject to any disclaimer, the term of this patent is extended or adjusted under 35 U.S.C. 154(b) by 1713 days.

(21) Appl. No.: 10/687,897

(22) Filed: Oct. 17, 2003

(65) Prior Publication Data
US 2004/0081680 A1     Apr. 29, 2004

Related U.S. Application Data

(63) Continuation of application No. PCT/US02/11911, filed on Apr. 16, 2002.

(30) Foreign Application Priority Data

Apr. 17, 2001   (EP) ..................................... 01109351

(51) Int. Cl.
A61F 13/00    (2006.01)
A61K 9/70     (2006.01)
A61K 9/00     (2006.01)
A61K 8/02     (2006.01)

(52) U.S. Cl. .......................... 424/443; 424/400; 424/401
(58) Field of Classification Search .................... 424/402
See application file for complete search history.

(56) References Cited

U.S. PATENT DOCUMENTS

| | | | |
|---|---|---|---|
| 3,896,807 A | 7/1975 | Buchalter | |
| 4,060,091 A | 11/1977 | Watson et al. | |
| 4,136,163 A | 1/1979 | Watson et al. | |
| 4,150,052 A | 4/1979 | Watson et al. | |
| 4,153,679 A | 5/1979 | Rowsell et al. | |
| 4,178,459 A | 12/1979 | Watson et al. | |
| 4,190,643 A | 2/1980 | Watson et al. | |
| 4,193,936 A | 3/1980 | Watson et al. | |
| 4,226,988 A | 10/1980 | Watson et al. | |
| 4,230,688 A | 10/1980 | Rowsell et al. | |
| 4,248,859 A | 2/1981 | Rowsell et al. | |
| 4,296,255 A | 10/1981 | Roswell et al. | |
| 4,318,900 A | 3/1982 | Rowsell et al. | |
| 4,713,068 A * | 12/1987 | Wang et al. ................... 604/366 |
| 4,844,883 A | 7/1989 | Patel | |
| 5,266,592 A * | 11/1993 | Grub et al. ................... 514/452 |
| 5,364,626 A | 11/1994 | Hasegawa et al. | |
| 5,370,764 A * | 12/1994 | Alikhan ........................ 156/553 |
| 5,451,404 A | 9/1995 | Furman | |
| 5,514,122 A * | 5/1996 | Morris et al. ................. 604/387 |
| 5,681,298 A | 10/1997 | Brunner et al. | |
| 5,756,857 A | 5/1998 | Kuribayashi et al. | |
| 5,769,833 A | 6/1998 | Hasse | |
| 5,830,487 A | 11/1998 | Klofta | |
| 5,968,025 A * | 10/1999 | Roe et al. ..................... 604/364 |
| 6,048,549 A * | 4/2000 | Nitikhunkasem et al. ..... 424/489 |
| 6,107,537 A * | 8/2000 | Elder et al. ..................... 604/364 |
| 6,471,984 B1 | 10/2002 | Hirashima et al. | |
| 6,503,526 B1 | 1/2003 | Krzysik et al. | |
| 6,506,958 B2 | 1/2003 | Williams | |
| 6,551,676 B1 | 4/2003 | Yamakawa et al. | |
| 6,761,947 B2 | 7/2004 | Yamakawa et al. | |
| 6,972,010 B2 | 12/2005 | Pesce et al. | |
| 7,166,307 B1 | 1/2007 | Ahn et al. | |
| 2003/0028163 A1 | 2/2003 | Lin | |
| 2004/0082654 A1 | 4/2004 | Pesce et al. | |
| 2004/0232024 A1 | 11/2004 | Guerreschi et al. | |
| 2005/0203473 A1 | 9/2005 | Pesce et al. | |

FOREIGN PATENT DOCUMENTS

| | | |
|---|---|---|
| DE | 26 08 226 A | 9/1977 |
| EP | 0 811 392 A1 | 12/1997 |
| EP | 1 040 802 A1 | 4/2000 |
| EP | 1 040 806 A1 | 4/2000 |
| EP | 0 997 144 A1 | 5/2000 |
| FR | 1 572 332 | 6/1969 |
| JP | 57-126416 | 6/1982 |
| JP | 64-066107 | 3/1989 |
| JP | 04-337395 | 11/1992 |
| JP | 05-255688 | 10/1993 |
| JP | 06-329528 | 11/1994 |
| JP | 08-176587 | 7/1996 |
| JP | 09-108261 | 4/1997 |
| JP | 2000-095679 | 4/2000 |
| JP | 2000-119132 | 4/2000 |
| JP | 2000-239142 | 9/2000 |
| JP | 2000-247859 | 9/2000 |

(Continued)

OTHER PUBLICATIONS

Scapin et al.(Use of triethylcitrate plasticizer in the production of poly-L-lactic acid implants with different degradation times, Journal of materials science, 2003, vol. 14 No. 7, pp. 635-640 [6 pages(s) article)].*
PCT International Search Report dated Aug. 21, 2002.
Office Action for U.S. Appl. No. 11/106,402; dated May 15, 2006.
Office Action for U.S. Appl. No. 11/106,402; dated Nov. 29, 2005.
Office Action for U.S. Appl. No. 11/106,402; dated Oct. 31, 2006.
Office Action for U.S. Appl. No. 10/687,687; dated Dec. 7, 2004.
Notice of Allowance for U.S. Appl. No. 10/687,687; dated Mar. 24, 2005.
Supplemental Notice of Allowability for U.S. Appl. No. 10/687,687; dated Sep. 23, 2005.
Office Action for U.S. Appl. No. 10/687,845; dated Oct. 25, 2006.
Office Action for U.S. Appl. No. 10/687,845; dated Feb. 21, 2007.
Office Action for U.S. Appl. No. 10/687,845; dated Jul. 19, 2007.

(Continued)

Primary Examiner — Sreeni Padmanabhan
Assistant Examiner — Timothy E Betton
(74) Attorney, Agent, or Firm — Andres E. Velarde; Amanda T. Barry; Jason J. Camp

(57) ABSTRACT

The present invention relates to articles to be worn in contact with a mammal body, such as sanitary napkins, pantiliners, nursing pads, baby diapers and the like. The article includes a mint odor-free cooling agent able to convey freshness sensation to the wearer of the article, without the need of modifying body surface temperature.

8 Claims, No Drawings

FOREIGN PATENT DOCUMENTS

| | | |
|---|---|---|
| WO | WO 96/14840 A1 | 5/1996 |
| WO | WO 96/16682 A1 | 6/1996 |
| WO | WO 97/45013 A1 | 12/1997 |
| WO | WO 98/26808 | 6/1998 |
| WO | WO 00/59436 | 10/2000 |
| WO | WO 00/64501 A1 | 11/2000 |
| WO | WO 00/64503 A1 | 11/2000 |
| WO | WO 01/24748 | 4/2001 |
| WO | WO 01/45615 A1 | 6/2001 |

OTHER PUBLICATIONS

Office Action for U.S. Appl. No. 10/687,845; dated Jan. 9, 2008.
Office Action for U.S. Appl. No. 10/687,845; dated Jul. 18, 2008.
Office Action for U.S. Appl. No. 10/831,725; dated Feb. 9, 2007.
Office Action for U.S. Appl. No. 10/831,725; dated Jul. 27, 2007.
Office Action for U.S. Appl. No. 10/831,725; dated Jan. 18, 2008.
Office Action for U.S. Appl. No. 10/831,725; dated Jul. 30, 2008.

* cited by examiner

US 8,273,367 B2

ARTICLES COMPRISING A MINT ODOR-FREE COOLING AGENT

CROSS REFERENCE TO RELATED REFERENCES

This is a continuation of International Application PCT/US02/11911 with an International filing date of Apr. 16, 2002.

FIELD OF THE INVENTION

The present invention relates to articles to be worn in contact with body of mammals, in particular to hygienic disposable absorbent articles like sanitary napkins, panty liners, tampons, incontinent pads, diapers, interlabial pads, breast pads, perspiration pads. More particularly, the present invention is directed to articles suitable to be worn in contact with mammal body, comprising a mint odor-free cooling agent able to stimulate thermo-receptors of the body surface of mammals to convey freshness sensation to the wearer of the article, without the need of modifying body surface temperature.

BACKGROUND OF THE INVENTION

Although articles to be worn in contact with human body, such as diapers for babies or sanitary napkins or panty liners for women have improved a lot the last years with respect to various features like protection and comfort in use, there is still a consumer need for further improvement namely making more pleasant the experience of wearing such articles, especially upon prolonged wearing periods.

It is thus an object of the present invention to provide articles to be worn in contact to mammal body, preferably human body, which makes the wearing experience more pleasant. It has now been found that improved pleasantness to the wearing experience can be achieved by providing noticeable freshness sensation, especially long lasting freshness sensation.

It is thus a particular object of the present invention to provide articles suitable to be worn in contact with human body that deliver improved comfort, especially freshness sensation and even long lasting freshness sensation.

It is a further object of the present invention to provide articles suitable to be worn in contact with human body, which deliver freshness sensation without wet feeling.

It is yet another object of the present invention to provide articles suitable to be worn in contact with skin and/or mucosal surface, which deliver freshness sensation while being safe to the skin and/or mucosal surface contacted.

It has now been found that these objects are achieved by providing an article, suitable to be worn in contact with mammal body, which article comprises a mint odor-free cooling agent to convey freshness sensation to the wearer of the article, without the need of modifying body surface temperature.

Mint-odor free cooling agents for use herein are typically selected from the group consisting of ketals, carboxamides, cyclohexanol derivatives, cyclohexyl derivatives described herein after with the exception of menthol and mixtures thereof. Highly preferred cooling agent for use herein is menthyl lactate. All these cooling agents beside their long lasting cooling properties have the advantage of being less irritating to skin than menthol, substantially free of mint-type odor and physically stable at room temperature. Indeed they do not sublimate at use and room temperature in contrast to menthol, thereby resulting in improved stability during storage of the article, maintaining the whole activity potential up to time it is needed, i.e., up to the time they are worn and during that time.

The use of cooling agents in articles to be worn in contact to human body, especially hygienic disposable articles (like sanitary napkin, panty liners, tampons, interlabial pads and/or diapers), delivers a freshness sensation without modifying skin and/or mucosal surface (e.g. vaginal area) temperature, this even upon prolonged periods of wearing time, thereby making the wearing experience of such articles more pleasant. Advantageously, these freshness properties are delivered without that any wet feeling is perceived on the contact of the article with skin and/or mucosal surface, resulting thereby in outstanding cleanness sensation. Furthermore, the perception of freshness and dryness sensation by the wearer of the article is believed to reduce the tendency of the wearer to perspire.

A further advantage is that the articles according of the present invention deliver all these benefits while being safe to the wearer. Indeed, the cooling agents described herein have a safe profile towards skin and mucosal surfaces. Yet another advantage is that all these benefits are delivered without strong mint-odor typically associated to the use of menthol and peppermint oil, which are not contemplated herein.

The cooling agents used in articles to be worn in contact with mammal body of the present invention, have the ability to cause a subjective sensation of freshness, without needing skin and/or mucosal surface temperature change. This sensation of freshness also called herein coolness/cooling sensation is attributed to the stimulation of thermo-receptors of mammal body. Indeed, it is believed that the cooling agents act as a direct stimulus on the cold receptors at the sensory nerve endings, which in turn stimulate the central nervous system. It is further noticeable that due to the persistence of the stimuli a long lasting freshness sensation is delivered, this even after stopping direct contact between the skin and/or mucosal surface and the article, more precisely the cooling agent.

The cooling agent may be present neat (powder, flakes, particles, wax, liquid and the like) or may be in a carrier vehicle as a solution, suspension, dispersion, emulsion and the like. Moreover the cooling agent may be releasably contained by a microcapsule, an absorbent material, a cell, an adhesive, an emollient-containing composition, a solid support, a nanophase particulate structure and the like. Indeed, in a preferred embodiment herein the article according to the present invention comprises a delivery system for releasably containing and delivering the cooling agent to at least a portion of the skin and/or mucosal surface of the wearer of the article. The delivery system may be of any configuration including, but not limited to, one that contains the cooling agent in powder, particle or flake form, or in a solution, a dispersion, a suspension, an emulsion or the like. The delivery system may comprise a structure such as a microcapsule, an absorbent material, a nanophase particulate structure, a cell, an adhesive, a solid support, or the like or a composition such as an emollient-containing composition. Preferably the delivery system is an emollient-containing composition. In one aspect of the invention the emollient-containing composition consists essentially of the emollient and the cooling agent without any additional compound. Preferably the delivery system positions the cooling agent in proximity to the skin during wear of the article and, more preferably, onto at least a portion of the skin and/or mucosal surface of the wearer of the article.

Advantageously, the presence of the emollient-containing composition delivers an optimized freshness sensation upon prolonged wearing time of the article while maintaining or even improving skin health. The presence of a delivery system, preferably emollient-containing composition, is desirable has it provides for faster freshness sensation/perception to the wearer of the article as well as sustained freshness sensation upon prolonged wearing time. Indeed, without to be bound by any theory it is speculated that the delivery system, namely emollient-containing composition (preferably ester derivatives as described herein after—for example triethyl citrate), acts as a carrier for the cooling agent as described herein, to help it migrate from its location in the article to the body surface of the wearer (skin and/or mucosal surface), penetrate the outer layers of the skin (stratum corneum) and bring it into direct and prolonged contact with the thermo receptors of mammal skin and/or mucosal surface. Actually, the delivery system, namely emollient-containing composition, like ester derivatives described herein after, helps the cooling agents to reach their target, namely thermo-receptors, in faster condition, thereby delivering a more immediate freshness sensation and maintain it in prolonged contact with the thermo receptors, thereby promoting long lasting freshness sensation as compared to the same article comprising the cooling agents at same level but neat. In other words, the presence of the delivery system, namely emollient-containing composition like ester derivatives described herein after, allows a controlled diffusion of the cooling agent, thereby resulting in a sustained freshness sensation even upon prolonged wearing time, typically up to a few hours, corresponding to usual wearing time of such articles. Furthermore, the presence of emollient moisturizes/hydrates and softens the skin and tends to reduce roughness, cracking and skin irritation.

Additionally the presence of such delivery system, namely the emollient-containing composition as described herein after, helps solubilisation of the cooling agent, thereby facilitating homogeneously application (if desired) of the cooling agent over at least a portion of the article. In a preferred embodiment herein the cooling agent is applied on the wearing facing surface of the article in a homogeneous way thereby further contributing to faster and sustained freshness sensation during prolonged wearing time of the article.

Yet a further advantage of the presence of such delivery system, namely the emollient-containing composition as described herein after, is its contribution to physical and chemical stability of the cooling agent during storage and use of the articles herein.

In a preferred embodiment herein the article according to the present invention is breathable, i.e., liquid vapor permeable and preferably air permeable. Indeed the breathability of the article further contributes to the freshness and dryness sensation, and especially to long lasting freshness and dryness sensation. Without to be bound by theory, it is speculated that the use of breathable article is able to maintain a more comfortable skin surface temperature over the skin surface which it covers, that is closer to the temperature of the skin surface when the consumer is not wearing such an article in contrast to non breathable article. This will provide a more ideal or 'normal' temperature perception in the genital region and hence contributes to the freshness sensation provided by the presence of the cooling agent in the article of the present invention. Also the breathability of the article reduces humidity at the article/skin interface and hence increases the dryness sensation. This increase in freshness and dryness sensation to the wearer results in outstanding cleanliness perception.

By using breathable articles, preferably breathable hygienic disposable articles, not only improved comfort (i.e., improved freshness and dryness sensation) to the wearer during use is provided but also reduction of malodour perception. It is believed that the breathable environment does not only contribute to the primary comfort benefit (freshness and dryness sensation) but also provides effective reduction or even prevention of malodor formation typically associated with body discharge onto the article worn into contact with human body. Indeed the breathability of the article, which reduces the hot, humid and anaerobic environment between the skin of the wearer and the surface of the article, contributes in an overall reduction of growth of microorganisms, known as being responsible of malodor formation. Furthermore, the reduction in the hot, humid and occlusive environment between the vicinity of the skin of the wearer and the article itself also reduces the tendency of the wearer to perspire. Consequently, the amount of associated perspiration related odour is reduced too.

In an embodiment herein the articles according to the present invention might comprise on top of the cooling agents any odor control agent (e.g., zeolite, silicate, silica, chelating agents, oxidizing agents, antimicrobial agents and the like). Such articles are particularly beneficial for further improving comfort and discretion in use.

The present invention is preferably directed to hygienic disposable articles like bandages, thermal pads, acne pads, cold pads, wrist cooler, compresses, surgical pads/wound dressings, protective bedding covers, protective clothing, gloves, socks, pillow covers, protective face masks, ornamental/fashionable articles or eye wear, prosthesis, plasters, wraps, hearing aids and the like, hygienic articles for absorbing perspiration such as perspiration pads, underarm sweat pads, shoe insoles, shirt inserts, sporting clothes, cap inside liner and the like, and hygienic articles for animals like litters as well as hygienic disposable absorbent articles for use by babies and adults like panty liners, feminine napkins, incontinent pads, diapers, tampons, interlabial pads, breast pads, human waste management devices and the like.

BACKGROUND ART OF THE INVENTION

In U.S. Pat. Nos. 5,649,914 and 5,797,892; a toilet training aid is disclosed which generates a heating or cooling effect in the presence of urine from the wearer within the article. The heating or cooling effect is intended to cause the wearer discomfort in an attempt to aid in the toilet training process. This heating or cooling effect performs no useful function upon the article itself. Instead, the toilet training aid acts upon the wearer to cause the wearer to take some action (i.e., remove the wet article and apply a new one). Further, the toilet training aid responds solely to conditions within the article itself, not to conditions between the article and the wearer. Further, the toilet training aid is only functioning for a short period of time and is not designed to provide a sustained reduction in relative humidity or temperature for typical wear times. EP 704 195 discloses sanitary napkins to be used as menstrual detector containing a temperature-sensitive reactive chemical. Example of such temperature-sensitive reactive chemical include sodium thiosulfate or sodium hyposulfite, which can respond by turning cold upon coming into contact with and dissolving in a hot liquid, such as a menstrual flow. This art on hygienic disposable absorbent articles mentioned herein before in no way teaches an effort to improve comfort of the wearer of such articles by conveying freshness sensation to the wearer of the articles, without the need of modifying body surface temperature.

Such physiological cooling agents that provide cooling sensation to skin and/or mucosal surfaces per se are known as well as their application in edible compositions like beverages and chewing-gum, in cosmetic products like shave lotions, deodorants, face creams, shampoos, toilet soaps and dentifrices, in tobacco preparations like cigars, cigarettes and chewing tabacco. See for example U.S. Pat. No. 5,451,404, U.S. Pat. No. 5,266,592 or DE 26 08 226. WO 96/14840 also discloses the use of menthyl lactate as pain reliever.

None of these prior art references discloses nor suggests articles suitable to be worn in contact with mammal body, namely hygienic disposable articles like sanitary napkin and/or panty liners, comprising a mint-odor free cooling agent able to convey freshness sensation, namely long lasting freshness sensation, to the wearer of the article, without the need of modifying body surface temperature, whereby improved comfort and discretion is delivered.

SUMMARY OF THE INVENTION

This invention encompasses articles suitable to be worn in contact with mammal body, preferably disposable hygienic articles, namely absorbent articles like sanitary napkins and/or panty liners, the articles comprising a mint-odor free cooling agent to convey freshness sensation to the wearer of the articles, without the need of modifying body surface temperature.

In a preferred embodiment the articles comprise a delivery system for containing and delivering the mint-odor free cooling agent to at least a portion of the skin and/or mucosal surface of a wearer of the article. Preferably the delivery system is an emollient-containing composition comprising an emollient on top of the cooling agent. The emollient-containing composition allows delivering more rapidly a freshness sensation to the wearer of the article upon contact of the article to the skin and/or mucosal surface while maintaining freshness sensation upon prolonged wearing time, typically during all the wearing time of the article, this while maintaining or even improving skin health.

In a preferred embodiment the article according the present invention is breathable. The breathability of the article which reduces the hot, humid and occlusive environment between the skin of wearer of the article and the article contributes to the freshness and dryness sensation, this upon prolonged wearing time, thereby resulting in outstanding cleanness feeling.

DETAILED DESCRIPTION OF THE INVENTION

By "article" it is meant herein any tridimentional solid or semi-solid substrate/material being able to comprise a mint-odor free cooling agent and being suitable to be worn in direct contact with mammal body, namely skin and/or mucosal surface of human body. By 'worn' it is meant herein article designated to be contacted and maintained in place for at least a few minutes and typically over one or several hours.

The term "disposable articles" is used herein to describe articles that are not intended to be launched or otherwise restored or reused as an article (i.e., they are intended to be discarded after a single use and, preferably to be recycled, composted or otherwise disposed of in an environmentally compatible manner).

As used herein, the term 'hygienic article' refers to various article of comfort and/or medical use, for the use by babies and adults or even animals.

The term "absorbent article" is used herein in a very broad sense including any article able to receive and/or absorb and/or contain and/or retain fluids and/or exudates, especially body fluids/body exudates. "Absorbent articles" as referred to herein include, without to be limited to, sanitary napkins, panty liners, incontinence pads, interlabial pads, tampons, breast pads, sweat-absorbent underarm pads, collar inserts, baby diapers, adult incontinence diapers, and human waste management devices. Typically such human urine or faecal management devices comprise a bag having an aperture and a flange surrounding the aperture for preferably adhesive attachment to the urogenital area and/or the perianal area of a wearer. Any faecal or urine management device known in the art is suitable for use herein. Such devices are described in for example WO 99/00084 to WO 99/00092.

As used herein, the term 'wearer-facing' surface refers to the surface of the component of the article generally oriented to face the wearer skin and/or mucosal surface during use of the article. As used herein, the term 'garment facing' surface refers to the opposite outer surface of the article, typically the surface directly facing the garment of a wearer, if worn in direct contact with garment.

As used herein, the term 'body fluids and/or body exudates' refers to any fluid/exudate produced by human or animal body occurring naturally or accidentally like for instance in the case of skin cutting, including for instance perspiration, urine, menstrual fluids, faeces, vaginal secretions and the like.

As used herein the term, 'maintain skin health' means to preserve the natural state of healthy skin. The term 'improve skin health' refers to a reduction in the extent of adverse skin effects. These terms describe skin health in the area covered by the articles. It will be recognized that the articles of the present invention maintain or even improve skin health in different regions of an individual wearer.

Mint Odor Free Cooling Agent

According to the present invention the articles comprise as an essential component a mint odor-free cooling agent able to convey freshness sensation to the wearer of the articles, without the need of modifying body surface temperature, or a mixture thereof.

By 'mint odor-free' cooling agent it is meant herein any cooling agent able to convey freshness sensation to the wearer of the article, without the need of modifying body surface temperature, which are less odorant than menthol or peppermint oil. In other words, which do not have the strong mint odour associated to menthol or peppermint oil. Accordingly by 'mint odor-free cooling agent' it is typically meant any cooling agent with the exception of menthol and/or peppermint oil.

Suitable cooling agents for use herein include all cooling agents for which the cooling effect (also called herein freshness effect) is a physiological effect due to the direct action of these agents on the nerve endings of the mammal body responsible for the detection of hot or cold without any occurrence of temperature change on the surface of the mammal body. It is believed that these agents act as a direct stimulus on the cold receptors at the nerve endings, which in turn stimulate the central nervous system. In this way a freshness sensation (also called herein cooling sensation) is simulated in absence of real change in skin temperature. Due to the persistence of the stimuli a long lasting cooling sensation is delivered even after removal of the cooling agent.

It is to be understood herein that the cooling sensation is personnel to a given individual. It must be admitted that skin tests are somewhat subjective, some individuals experiencing a greater or lesser cooling sensation than others when subjected to the same test. The cooling perception depends on the density of thermo-receptors on skin and on the skin thickness. Typically it is observed that the thinner the skin is the more intense is the cooling sensation (also called herein freshness sensation). Without to be bound by any theory, it is believed that the thinner the skin is, the more rapid is the penetration of the cooling agent through the skin and higher is the absorption level thereof. Furthermore studies have demonstrated that geographic factors and/or races further play a role in freshness perception.

Without to be bound by theory, it is speculated that the cooling agents are able to penetrate through the skin surface and depolarize (clear the potential differential between the inside and outside nervous cell membranes by blocking calcium ion exchange) the membrane of cold receptors. The cold perception is the result of the depolarization.

More particularly, it is believed that due to binding calcium properties of the cooling agents, the equilibrium between the concentration of calcium ion outside and inside the nervous cell membrane is disturbed. In other words by reducing the calcium ion level outside the nervous cell membrane, the membrane is depolarized, resulting thereby in increased discharge rate of nerve fibers and hence transfer of electrical stimuli to central nervous system.

Without to be bound by any theory, it is believed that the long lasting effect is linked to binding stability properties of the cooling agent and calcium ion complex. The higher is the stability of the complex cooling agent-calcium ion, the longer the calcium is linked to the cooling agent, the longer is the resulting freshness sensation.

Studies performed on cooling agent activity have showed that four features of the molecular structure of the cooling agents are particularly important to deliver freshness/cooling sensation.

Reference is made to H. R. Watson et al., Journal of the Society of Cosmetic Chemist, Vol. 29, p185-200, 1978, incorporated herein per reference.

Suitable cooling agents for use herein posses the following properties:

a hydrogen binding function—The cooling agents apparently need to have an atom or group able to bind hydrogen. The stronger the molecule's hydrogen binding capacity, the stronger the cooling effect. However, the presence of more than one hydrogen-binding group in its molecule can reduce its cooling effect, as the molecule would no longer have the correct lipophilic characteristics;

a compact hydrocarbon skeleton such that the body's thermo-receptors are able to 'recognize' them;

a balance between their hydrophilic and hydrophobic parts for both delivering cooling properties and able them to penetrate the biological membrane such as outer skin layers—The most common method of determining this balance is to use the Hansch log P value—the coefficient of water and n-octanol distribution according to Hansch. The log P value is acknowledged as being a crucial factor in a substance's pharmacological activity—especially as regards how it is transported through skin. The log p values of preferred cooling agents for use herein generally lies somewhere between 2.0 and 3.0;

typically a molecular weight of between 150 and 350.

Particularly suitable cooling agents to be used herein being free of the mint odor associated to menthol/peppermint oil include ketals, carboxamides, cyclohexanol derivatives and/or cyclohexyl derivatives with the exception of menthol. Advantageously all these compounds have safer profile to skin than menthol/peppermint oil, which are known (especially at high concentration) to cause burning and itching sensation to skin.

Ketals:

Ketals suitable for use herein are according to the following formula:

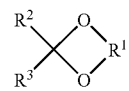

(I)

in which $R^1$ represents a $C_2$-$C_6$-alkylene radical having at least 1, but not more than 3, hydroxyl group(s), preferably one hydroxyl group, and either $R^2$ and $R^3$ independently of one another represent $C_1$-$C_{10}$-alkyl which is optionally substituted by 1 to 3 radicals selected from the group comprising hydroxyl, amino and halogen (such as fluorine, chlorine, bromine or iodine), $C_5$-$C_7$-cycloalkyl, preferably cyclohexyl, $C_6$-$C_{12}$-aryl, preferably phenyl, with the proviso that the total of the C atoms of $R^2$ and $R^3$ is not less than 3, or $R^2$ and $R^3$ together represent an alkylene radical which, together with the carbon atom which carries the radicals $R^2$ and $R^3$, forms a 5-7-membered ring, it being possible for this alkylene radical, in turn, to be substituted by $C_1$-$C_6$-alkyl groups.

Preferred radicals $R^2$ and $R^3$ comprise methyl, isopropyl and tert-butyl.

The length of the radicals $R^2$ and $R^3$ influences the effect of the compounds I: shorter radicals lead to an immediate, short effect; longer radicals lead to a delayed, but prolonged effect. When solubility of the compounds in water is desired it is preferable to use the compounds with short radicals $R^2$ and $R^3$.

Preferred radicals $R^1$ embrace 1,2- and 1,3-alkylene radicals, which, together with the two oxygen atoms and with the carbon atom to which the two oxygen atoms are attached, form a dioxolane or dioxane ring.

Preferred compounds I in which $R^2$ and $R^3$ together represent an alkylene radical are those of the formula

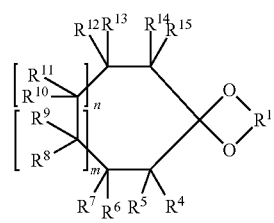

(Ia)

in which $R^4$ to $R^{15}$ independently of one another denote hydrogen or $C_1$-$C_6$-alkyl, preferably hydrogen or $C_1$-$C_4$-alkyl, and m and n independently of one another denote zero or 1.

Preferred compounds of the formula Ia are those in which the total of m+n is 1, i.e. ketals of an optionally substituted cyclohexanone.

Preferred substituents, of which there may be present, in particular, 1 to 3, are methyl, isopropyl and tert.-butyl.

The ketals I can be prepared by known processes. For example, ketal I will generally be prepared by acid-catalysed reaction of the ketone on which ketal I is based and not less than the equivalent amount of aliphatic $C_3$-$C_6$-alcohol having not less than 3 and not more than 5, preferably 3, hydroxyl groups. In general, the ketone on which ketal I is based and not less than 0.5 tool equivalents, but, as a rule, a 1.2- to 4-fold, preferably 1.5- to 3-fold excess of this amount of the $C_3$-$C_6$-alcohol having 3 to 5 hydroxyl groups will be employed. Examples of acid catalysts, which can be used, are p-toluenesulphonic acid, phosphoric acid or potassium hydrogen sulphate in catalytically effective amounts (for example 0.1 to 3 g of p-toluenesuphonic acid per mole of ketone). The reaction will preferably be carried out either in an organic solvent, which together with water forms an azeotrope, so that the water, which is liberated during the formation of the ketal, can be eliminated by azeotropic entrainment, or water-consuming core agents such as, for example, trialkyl ortho esters are used. Examples of preferred organic solvents comprise benzene, toluene, xylene, chloroform, methylene chloride and trichloroethylene.

The reaction can be regarded as complete when water no longer separates out or when an ester/alcohol mixture is no longer separated out. It is recommended to wash the products subsequently with dilute alkali and with water, to separate and dry the organic phase, to strip off the solvent and, if appropriate, to purify the residue, for example by distillation.

Particularly preferred ketals I are those of the formulae

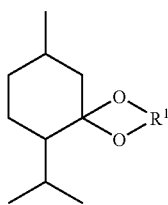

(II)

(III)

(IV)

(V)

(VI)

in which $R^1$ has the abovementioned meaning.

Particularly preferred ketals are the ketals II.

The ketals I to be employed herein can have asymmetric C atoms; optical isomerism can therefore occur. Depending on the starting material and the preparation methods used, they can exist in the form of mixtures of the optical isomers or in the form of pure isomers. The cooling effect of the isomers may differ, so that one or the other isomer may be preferred.

These ketals are for example described and exemplified in U.S. Pat. No. 5,266,592, incorporated herein by reference in its entirety.

An example of ketal commercially available include a ketal of formula (II) above, where $R^1$ is ethyl-(2 hydroxymethyl), namely menthone glycerol Ketal, available from Haarmann & Reimer GmbH (Germany) under the name Frescolat MGA.

Carboxamides

The carboxamides found most useful to be used herein are those described in U.S. Pat. No. 4,136,163, Jan. 23, 1979 to Wason et al., and U.S. Pat. No. 4,230,688, Oct. 28, 1980 to Rawsell et al. Both incorporated herein by reference in their entirety.

Particularly suitable carboxamides for use herein are N-substituted-p-menthane3-carboxamides (U.S. Pat. No. 4,136,163). These compounds are 3-substituted-p-menthanes of the formula:

[structure with CONR'R'']

where R', when taken separately, is hydrogen or an aliphatic radical containing up to 25 carbon atoms; R" when taken separately is hydroxy, or an aliphatic radical containing up to 25 carbon atoms, with the proviso that when R' is hydrogen R" may also be an aryl radical of up to 10 carbon atoms and selected from the group consisting of substituted phenyl, phenalkyl or substituted phenalkyl, naphthyl and substituted naphthyl, pyridyl; and R' and R", when taken together with the nitrogen atom to which they are attached, represent a cyclic or heterocyclic group of up to 25 carbon atoms, e.g. piperidino, morpholino etc.

In the above definitions "aliphatic" is intended to include any straight-chained, branched-chained or cyclic radical free or aromatic unsaturation, and thus embraces alkyl, cycloalkyl, alkenyl, cycloalkenyl, alkynyl, hydroxyalkyl, acyloxyalkyl, alkoxy, alkoxyalkyl, aminoalkyl, acylaminoalkyl, carboxyalkyl and similar combinations.

Typical values for R' and R" when aliphatic are methyl, ethyl, propyl, butyl, isobutyl, n-decyl, cyclopropyl, cyclohexyl, cyclopentyl, cycloheptylmethyl, 2-hydroxyethyl, 3-hydroxy-n-propyl, 6-hydroxy-n-hexyl, 2-aminoethyl, 2-acetoxyethyl, 2-ethylcarboxyethyl, 4-hydroxy-2-butynyl, carboxymethyl etc. When R" is aryl typical values are benzyl, naphthyl, 4-methoxyphenyl, 4-hydroxyphenyl, 4-methylphenyl, 3-hydroxy-4-methylphenyl, 4-fluorophenyl, 4-nitrophenyl, 2-hydroxynaphthyl, pyridyl, etc.

Other suitable carboxamides for use herein are certain acyclic tertiary and secondary carboxamides disclosed in U.S. Pat. No. 4,230,688, incorporated herein by reference. These have the structure $$R_2-\underset{\underset{R_3}{|}}{\overset{\overset{R_1}{|}}{C^*}}-CONR'R''$$

where R' and R", when taken separately, are each hydrogen, $C_1$-$C_5$ alkyl or $C_1$-$C_8$ hydroxyalkyl and provide a total of no more than 8 carbon atoms, with the proviso that when R' is hydrogen R" may also be alkylcarboxyalkyl of up to 6 carbon atoms.

R' and R", when taken together, represent an alkylene group of up to 6 carbon atoms, the opposite ends of which group are attached to the amide nitrogen atom thereby to form a nitrogen heterocycle, the carbon chain of which may optionally be interrupted by oxygen.

$R_1$ is hydrogen or $C_1$-$C_5$ alkyl; and $R_2$ and $R_3$ are each $C_1$-$C_5$ alkyl; with the provisos that (i) $R_1$, $R_2$ and $R_3$ together provide a total of at least 5 carbon atoms, preferably from 5-10 carbon atoms; and (ii) when $R_1$ is hydrogen, $R_2$ is $C_2$-$C_5$ alkyl and $R_3$ is $C_3$-$C_5$ alkyl and at least one of $R_2$ and $R_3$ is branched, preferably in an alpha or beta position relative to the carbon atom marked (*) in the formula.

Where the compounds used have an asymmetric carbon atom either optical isomer may be used in pure form but generally a mixture of optical isomers will be used. In some cases the degree of cooling produced by the compounds on the skin will differ as between optical isomer, in which case one or other isomer may be preferred.

The preferred carboxamides used herein are the tertiary compounds, i.e., those wherein each of $R_1$, $R_2$ and $R_3$ is $C_1$-$C_5$ alkyl, especially those where $R_1$ is methyl, ethyl or n-propyl and at least one of $R_2$ and $R_3$ is a branched chain group having branching in an alpha or beta position relative to the C atom marked (*) in the formula. Also preferred are mon-substituted amides, i.e. where R' is H, and disubstituted amides where R' and R" are methyl or ethyl. A further preferred group consists of amides of the formula given where $R_1$ is hydrogen and at least one of $R_2$ and $R_3$ is branched in an alpha position relative to the carbon atom marked * in the formula.

The carboxamides may readily be prepared by conventional techniques, for example, by reaction of an acid chloride of the formula $R_1 R_2 R_3$ COCl with an amine of the formula HNR'R" in the presence of a hydrogen chloride acceptor. Such reactions are entirely conventional and the procedures involved will readily be understood by the persons skilled in the art.

Particularly suitable carboxamides for use herein are monosubstituted tertiary amides of the formula:

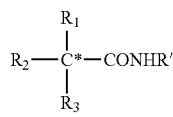

wherein $R_1$, $R_2$ and $R_3$ are each $C_1$-$C_5$ alkyl and together provide a total of at least 5, preferably 5-10 carbon atoms; and R' is $C_1$-$C_5$ alkyl, $C_1$-$C_8$ hydroxyalkyl or alkylcarboxyalkyl of up to 8 carbon atoms. In this group $R_1$ is preferably methyl, ethyl or n-propyl and one or both of $R_2$ and $R_3$ is branched in an alpha or beta position relative to the carbon atom marked (*).

An example of such aliphatic carboxamides is methyl-(N, 2,3 tri-methyl)-2-isopropyl butanamide commercially available from IFF (International Flavors &Fragrances-US) under the name WS-23®. An example of such cyclic carboxamides is ethyl menthane carboxamide commercially available from Rhodia Chirex (UK) under the name WS-3®.

Cyclohexanol Derivatives

Suitable cyclohexanol derivatives for use herein are represented by the following general formula:

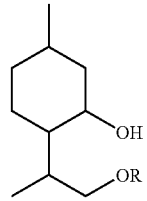

(1)

wherein R represents a linear or branched alkyl group having 1 to 5 carbon atoms.

The formal nomenclature thereof is 2-(2-alkoxy-1-methylethyl)-5-methyl-cyclohexanol. The above compound has a plurality of stereoisomers. Although any of them has strong refrigerating activity and is practically odorless, a cyclohexanol derivative represented by the following general formula:

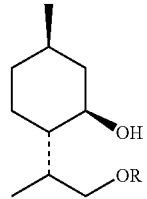

(1a)

wherein R represents a linear or branched alkyl group having 1 to 5 carbon atoms, namely (1R,2S,5R,8R)-2-(2-alkoxy-1-methylethyl)-5-methylcyclohexanol is preferred from the viewpoint of, for example, the continuity of cooling sensation.

Suitable cyclohexanol derivatives for use herein also include those of following general formula:

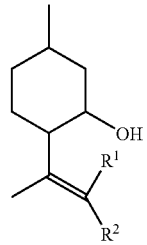

(2)

wherein $R^1$ and $R^2$ are independently hydrogen, or a linear or branched alkyl group having 1 to 5 carbon atoms.

Examples of the linear or branched alkyl groups each having 1 to 5 carbon atoms represented by R in the above general formulae (1) and (1a) or by $R^1$ and $R^2$ in formulae (2), include methyl, ethyl, n-propyl, isopropyl, n-butyl, isobutyl, sec-butyl, tert-butyl, n-pentyl, isopentyl, sec-pentyl, tert-pentyl and neopentyl groups. Of these, methyl, ethyl, isopropyl, tert-butyl and n-pentyl groups are preferred, and a methyl group is especially preferred.

These compounds are described in more details including process of making them in U.S. Pat. No. 5,756,857, herein incorporated as reference.

An example of commercially available cyclohexanol derivatives of formulae (2) above is 5-methyl-2-(1-methylethenyl) available from Takasago (Japan) under the name Coolact P®.

Cyclohexyl Derivatives

Suitable cyclohexyl derivatives for use herein are represented by the following general formula:

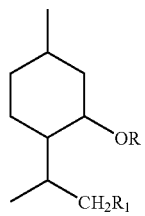

wherein R represents —H, a linear or branched alkyl group, alkenyl group, alkoxy group or acyloxy group having from 1 to 5 carbon atoms, $R_1$ represents —H, or a linear or branched alkyl group having from 1 to 5 carbon atoms, with the exception of compounds wherein both R and $R_1$ are hydrogen.

The above compound has a plurality of stereoisomers. Although any of them has strong refrigerating activity and is practically odorless, with the exception of those wherein both R and $R_1$ are hydrogen (i.e., menthol), cyclohexyl derivatives represented by the following general formula are preferred for use herein from the viewpoint of, for example, the continuity of cooling sensation.

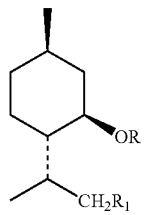

Highly preferred compounds are those of formula above wherein $R_1$=H and R is propanediol, carboxy-hydroxyethyl or carboxy hydroxypropyl. An example of these compounds is menthoxypropanediol available from Takasago under name TK10®

Highly preferred cyclohexyl derivative is menthyl lactate. Menthyl lactate is according to following formula:

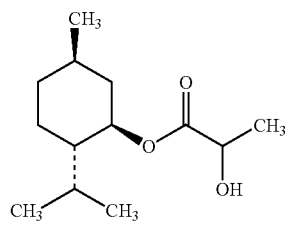

This compound is commercially available from Haarmann & Reimer GmbH (Germany) under the name FRESCOLAT, Type ML. It can also be readily made by processes known in the art by esterifying the hydroxy group of menthol with lactic acid. Two thirds of its molecular weight is attributable to the menthol moiety. Methyl lactate is virtually odorless, not suffering from the 'mint note' that otherwise customary in the case of menthol or peppermint oil. Advantageously this material has been found to be useful as topical pain reliever (see WO96/14840 incorporated herein by reference).

Other suitable cooling agents for use herein also include camphor, borneol eucalyptol, methyl salicylate, tea tree oil and/or, eucalyptus oil and plant extracts containing one or more of these compounds.

The articles of the present invention comprise an amount of the cooling agent sufficient to stimulate the thermo-receptors in the areas of the skin and/or mucosal surfaces with which the articles come into contact and thereby to convey the desired freshness sensation. As the degree and longevity of the freshness sensation varies from compounds to compounds the quantity of agents used in each article to be worn in contact with skin and/or mucosal surface of body will vary widely.

Typically, the articles of the present invention like hygienic disposable absorbent articles comprise on at least a portion of the article, the cooling agent or a mixture thereof at a level of from 0.01 $gm^{-2}$ to 300 $gm^{-2}$, preferably from 0.05 to 200 $gm^{-2}$, more preferably from 1 $gm^{-2}$ to 100 $gm^{-2}$ and most preferably from 2 $gm^{-2}$ to 20 $gm^{-2}$ per article.

The present invention is based on the finding that the presence of mint odor-free cooling agents, preferably the ketals, carboxamides, cyclohexanol derivatives, cyclohexyl derivatives or mixtures thereof as described herein, in articles to be worn in contact with skin and/or mucosal surfaces, provides the user with a freshness and dryness feeling, without the need of modifying external temperature conditions. Advantageously the articles with the mint odor-free cooling agent as described herein before give the user a comfortable freshness and dryness sensation upon prolonged wearing time of the articles, without any sensation of skin itchiness or skin burning.

Delivery System

Preferably the cooling agent may be releasable incorporated into any delivery system known to those skilled in the art that directly or indirectly facilitates the transfer of the cooling agent to the skin of the wearer of the article for perception of freshness sensation by the wearer of the article. The delivery system may contain the cooling agent neat, as a powder, flake or particulate form, wax, liquid or in a carrier vehicle as a solution, suspension, dispersion, emulsion or composition. When released from the delivery system the cooling agent is free to migrate from the location of the delivery system in the article to the skin and/or mucosal surface of the wearer. The delivery system may be a component of any portion or portions of the article including, but not limited to, in the event of hygienic absorbent articles, the topsheet, the backsheet, the absorbent core, any secondary layer(s) intermediate the core and sheet layers, the leg cuff, the side panel, the waist region, the fastener, the wings, an insertable element such as an absorbent material inserted into the absorbent article for use during wear of the article, specialized structures such as those employed to contain bowel movements (e.g., bowel movement "pockets"), and the like. Preferably the delivery system is positioned in proximity to the wearer's skin and, more preferably is a component of a wearer-facing surface of portions of the article such as the topsheet, side panels, leg cuffs, waist region, fasteners, wings and the like.

When the cooling agent is released by the delivery system it may be in an active functional form such as in a solution, dispersion, suspension, emulsion or the like, or it may be non-functional such as in powder, wax, flake or particulate form and activated by contact with moisture from urine and feces or other known means.

The types of delivery systems that are useful in the articles of the invention for facilitating automatic transfer of the cooling agent from any portion of the article to the skin and/or mucosal surface of a wearer will be readily apparent to those skilled in the art.

Exemplary delivery systems include, for example, pressure-rupturable or dissolvable microcapsules that are induced to express the cooling agent or cooling agent composition upon dissolving due to contact with moisture from bodily fluid, or rupturing due to pressure from the body or manual rupturing by a user prior to applying the article to a wearer. For example, a water-soluble film that encloses and expresses a powder upon contact with moisture is described in U.S. Pat. No. 4,790,836 and would be a suitable material for use in microcapsules containing the cooling agent in any form such as a powder, particulate, liquid or semi-solid. Examples of pressure-rupturable microcapsules suitable for containing the cooling agent are described in U.S. Pat. No. 3,585,998. Such microcapsules may be present in any portion of the article, including the wearer-facing surface. U.S. Pat. No. 4,623,339 describes an insertable layer that is removable from an article prior to use and manually pressure activatable to express a substance through slits in the layer. The disclosures of each of the foregoing patents are hereby incorporated by reference.

Other suitable delivery systems for containing the cooling agent or the cooling agent-composition include, but are not limited to, "cells" in the article that are enclosed or partially enclosed voids, regularly or irregularly shaped, that release the cooling agent when in contact with moisture, heat or pressure; and water-soluble adhesives and other such compositions which release the cooling agent upon contact with moisture, and the like.

Regardless of the delivery system employed, the cooling agent or cooling agent-containing composition upon release may be migrable from its original location, e.g., it may be moved by the flow of body fluid, by motion of the wearer, by pressure and the like, or because of a decrease in viscosity upon exposure to body heat, to other regions in the article. Cooling agents that are hydrophilic or are incorporated into vehicles that are hydrophilic may migrate throughout hydrophilic structures of the article, such as through hydrophilic pores or other openings that allow body fluid to flow from the topsheet to the core. Preferably, however, the delivery systems containing cooling agents are positioned in proximity to the skin of the wearer.

Other delivery systems suitable herein also include a wide variety of carrier vehicles. Carrier vehicles for the cooling agent include compositions that are in the form of lotions, creams, oils, ointments, powders, emulsions, foams, or gels. Typical carrier vehicles for the cooling agents include aqueous or alcoholic solutions, oils and fats such as hydrocarbon oils, fatty acid esters, long chain alcohols and silicone oils, finely divided solids such as starch or talc and the like.

In a preferred embodiment, the cooling agents are dissolved, suspended or emulsified components of emollient-containing compositions that can be positioned anywhere in the articles, but preferably are incorporated into a wearer-facing surface of the articles, such as the topsheet, wings, leg cuff, fastening device and the like of hygienic disposable absorbent articles.

Suitable emollient-containing compositions for containing and delivering the cooling agent are described further below.

In such a preferred embodiment, the emollient-containing composition comprises 0.1% to 99.9%, preferably from 3% to 90%, more preferably from 5% to 60%, and most preferably from 10% to 40% by weight of the cooling agent or mixture thereof, and from 99.9% to 0.1%, preferably from 97% to 10%, more preferably 95% to 40%, and most preferably from 90% to 60% by weight of the emollient or mixture thereof.

Highly preferred herein the emollient-containing composition consists of the cooling agent or a mixture thereof together with an emollient or a mixture thereof.

In addition to its function as a vehicle for delivering an effective concentration of a cooling agent to a wearer's skin, the emollient composition is particularly beneficial to skin, it improves skin hydratation and softness, and hence maintains or even improves skin health. Suitable emollients to be used herein assure a film-forming capacity on the skin, which gives emolliency and helps prevent skin dehydration when directly contacting the skin, thereby reducing or even eliminating the occurrence of skin itching or burning. Suitable emollients to be used herein are also able to locate themselves between the layers of the epiderm (thanks to their similarity with substances naturally contained in the epiderm (stratum corneum)), enhancing thereby the elastic properties of the skin.

The presence of an emollient, especially ester derivatives as described herein after, results in optimum freshness profile during wearing of the articles. The freshness sensation is not only delivered more quickly upon wearing of the article, but also is sustained/controlled over longer periods of time, as compared to a similar article with same level of cooling agent but in absence of such an emollient (typically ester derivatives like triethyl citrate). Without to be bound by any theory, it is believed that the presence of the emollient solubilises the cooling agent helping it to penetrate more quickly through the outer layer(s) of the skin and/or mucosal surface to make it readily available to the thermo-receptors. Furthermore the emollient due to its high affinity to skin and/or mucosal surface, deposits on the skin and remains into contact and within the skin/mucous for prolonged periods of time, allowing thereby diffusion of the cooling agent through the skin upon prolonged periods of time, this results in further long lasting freshness feeling.

The emollient-containing composition may be in a variety of forms, including, but not limited to, emulsions, dispersions, suspensions, gels, wax and the like.

In order to deliver an effective concentration of the cooling agent to the skin via an article over time, an effective amount of the emollient-containing composition containing the cooling agent that is applied to or migrated to one or more of the wearer-facing surfaces of the article depends, to a large extent on the emollient used.

The quantity of the emollient-containing composition on at least a portion of the wearer-facing surface of the article preferably ranges from 0.5 g/m² to 250 g/m², more preferably from 4 g/m² to 80 g/m², still more preferably from 8 to 40 g/m².

As discussed further hereinafter, the emollient-containing compositions useful for transferring cooling agents to the skin of the wearer preferably, though not necessarily, have a melting profile such that they are relatively immobile and localized on the wearer-facing surface of the article at room temperature, are readily transferable to the wearer at body temperature, and yet are not completely liquid under extreme storage conditions. Preferably, the compositions are easily transferable to the skin by way of normal contact, wearer motion, and/or body heat. Because the composition preferably is substantially immobilized on the article's wearer-facing surface, relatively low levels of composition are needed to impart the desired benefits.

In one embodiment, the emollient-containing compositions useful herein are water-in-oil emulsions, wherein the cooling agent is in solution or suspension in either the aqueous phase or the oil phase. However, the emollient-containing composition itself may be solid or more often semi-solid, at 20° C., i.e. at ambient temperatures. By "semisolid" is meant that the composition has a rheology typical of pseudoplastic or plastic liquids. When no shear is applied, the compositions can have the appearance of a semi-solid but can be made to flow as the shear rate is increased. This is due to the fact that, while the composition contains primarily solid components, it also includes a liquid component.

Preferred compositions are at least semi-solid at room temperature to minimize composition migration before wear of the article. In addition, the compositions preferably have a final melting point (100% liquid) above potential "stressful" storage conditions that can be greater than 45° C. (e.g., warehouse in Arizona, car trunk in Florida, etc.). Specifically, preferred compositions will have the following melt profile:

| Characteristic | Preferred Range | Most Preferred |
|---|---|---|
| % liquid at room temp. (20° C.) | 2-50 | 3-25 |
| % liquid at body temp. (37° C.) | 25-95 | 30-90 |
| final melting point (° C.) | 38 | 45 |

By being solid or semisolid at ambient temperatures, preferred emollient-containing compositions containing the cooling agent do not have a tendency to flow and migrate to a significant degree to undesired locations of the article to which they are applied. This means less composition is required for imparting desirable refreshing and skin care benefits.

As used herein, the term "emollient" is a material that protects against wetness or irritation, softens, soothes, supples, coats, lubricates, moisturizes, protects and/or cleanses the skin. (It will be recognized that several of the monographed actives listed above are "emollients", as that term is used herein.) In a preferred embodiment, these emollients will have either a plastic or liquid consistency at ambient temperatures, i.e., 20° C.

Representative emollients useful in the present invention include, but are not limited to, emollients that are petroleum-based; sucrose ester fatty acids; polyethylene glycol and derivatives thereof; humectants; fatty acid ester type; alkyl ethoxylate type; fatty acid ester ethoxylates; fatty alcohol type; polysiloxane type; propylene glycol and derivatives thereof; glycerine and derivatives thereof, including glyceride, acetoglycerides, and ethoxylated glycerides of $C_8$-$C_{28}$ fatty acids; spermaceti or other waxes; fatty acids, particularly those having from 8 to 28 carbon atoms in their fatty chain, such as mirytol; fatty alcohol ethers, particularly those having from 8 to 28 carbon atoms in their fatty chain, such as cetiol, stearic acid; propoxylated fatty alcohols; other fatty esters of polyhydroxy alcohols; lanolin and its derivatives; kaolin and its derivatives; sorbitol and its derivatives; trihydroxy stearin; or mixtures of these emollients.

Suitable petroleum-based emollients include those hydrocarbons, or mixtures of hydrocarbons, having chain lengths of from 16 to 32 carbon atoms. Petroleum based hydrocarbons having these chain lengths include mineral oil (also known as "liquid petrolatum") and petrolatum (also known as "mineral wax," "petroleum jelly" and "mineral jelly"). Mineral oil usually refers to less viscous mixtures of hydrocarbons having from 16 to 20 carbon atoms.

Suitable fatty acid ester type emollients include those derived from $C_8$-$C_{28}$ fatty acids, preferably $C_{12}$-$C_{22}$ saturated fatty acids, and short chain ($C_1$-$C_8$, preferably $C_1$-$C_3$) monohydric alcohols. Representative examples of such esters include methyl palmitate, methyl stearate, isopropyl laurate, isopropyl myristate, isopropyl palmitate, ethylhexyl palmitate and mixtures thereof. Suitable fatty acid ester emollients can also be derived from esters of longer chain fatty alcohols ($C_{12}$-$C_{28}$, preferably $C_{12}$-$C_{16}$) and shorter chain fatty acids e.g., lactic acid, such as lauryl lactate and cetyl lactate.

Suitable alkyl ethoxylate type emollients include $C_8$-$C_{22}$ fatty alcohol ethoxylates having an average degree of ethoxylation of from about 2 to about 30. Preferably, the fatty alcohol ethoxylate emollient is selected from the group consisting of lauryl, cetyl, and stearyl ethoxylates, and mixtures thereof, having an average degree of ethoxylation ranging from about 2 to about 23. Representative examples of such alkyl ethoxylates include laureth-3 (a lauryl ethoxylate having an average degree of ethoxylation of 3), laureth-23 (a lauryl ethoxylate having an average degree of ethoxylation of 23), ceteth-10 (a cetyl alcohol ethoxylate having an average degree of ethoxylation of 10) and steareth-10 (a stearyl alcohol ethoxylate having an average degree of ethoxylation of 10).

Suitable fatty alcohol type emollients include $C_9$-$C_{22}$ fatty alcohols, preferably $C_{16}$-$C_{18}$ fatty alcohols. Representative examples include cetyl alcohol and stearyl alcohol, and mixtures thereof.

Other suitable types of emollients for use herein include polysiloxane compounds. In general, suitable polysiloxane materials for use in the present invention include those having monomeric siloxane units of the following structure:

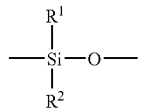

wherein, $R^1$ and $R^2$, for each independent siloxane monomeric unit can each independently be hydrogen or any alkyl, aryl, alkenyl, alkaryl, arakyl, cycloalkyl, halogenated hydrocarbon, or other radical. Any of such radicals can be substituted or unsubstituted. $R^1$ and $R^2$ radicals of any particular monomeric unit may differ from the corresponding functionalities of the next adjoining monomeric unit. Additionally, the polysiloxane can be either a straight chain, a branched chain or have a cyclic structure. The radicals $R^1$ and $R^2$ can additionally independently be other silaceous functionalities such as, but not limited to siloxanes, polysiloxanes, silanes, and polysilanes. The radicals $R^1$ and $R^2$ may contain any of a variety of organic functionalities including, for example, alcohol, carboxylic acid, phenyl, and amine functionalities. Exemplary alkyl radicals are methyl, ethyl, propyl, butyl, pentyl, hexyl, octyl, decyl, octadecyl, and the like. Exemplary alkenyl radicals are vinyl, allyl, and the like. Exemplary aryl radicals are phenyl, diphenyl, naphthyl, and the like. Exemplary alkaryl radicals are toyl, xylyl, ethylphenyl, and the like. Exemplary aralkyl radicals are benzyl, alpha-phenylethyl, beta-phenylethyl, alpha-phenylbutyl, and the like. Exemplary cycloalkyl radicals are cyclobutyl, cyclopentyl, cyclohexyl, and the like. Exemplary halogenated hydrocarbon radicals are chloromethyl, bromoethyl, tetrafluorethyl, fluorethyl, trifluorethyl, trifluorotloyl, hexafluoroxylyl, and the like.

Suitable fatty ester type emollients also include polyolpolyesters as described in U.S. Pat. No. 5,609,587, issued to Roe on Mar. 11, 1997, the disclosure of which is incorporated herein by reference. Exemplary polyols include, but are not limited to, polyhydric compounds such as pentaerythritol; sugars such as raffinose, maltodextrose, galactose, sucrose, glucose, xylose, fructose, maltose, lactose, mannose and erythrose; and sugar alcohols such as erythritol, xylitol, malitol, mannitol and sorbitol. Such polyols are esterified with fatty acids and/or other organic radicals having at least two carbon atoms and up to 30 carbon atoms. While it is not necessary that all of the hydroxyl groups of the polyol be esterified, preferred polyolpolyester emollients of the present invention have substantially all (e.g. at least about 85%) of the hydroxyl groups esterified. Particularly preferred are sucrose polyolpolyesters such as sucrose polycottonate, sucrose polysoyate, and sucrose polybehenate. Mixtures of such polyolpolyesters are also suitable emollients for the present invention.

Highly preferred emollients for use herein are the ester, alcohol or acid derivatives of below formulae.

Advantageously, beside their emolliency properties, these derivatives, especially the ester derivatives can function as enzyme substrates, which, when acted upon by a hydrolyzing enzyme typically present in body fluid, will be hydrolyzed resulting in the release of free acids. The presence of these acids will lower the pH of the area where the esters are topically applied to. This will amount to inactivation of all or most enzymes present in this area and resulting from contact of this area with body exudates, such as the lipase enzymes, protease enzymes and the like. This effect is relatively long lasting. In other words, the presence of such esters (especially those of formulae (II) or (III) herein after) not only provides optimized freshness sensation profile (including delivery of not only faster but also sustained/controlled freshness sensation upon prolonged wearing time of the articles), but reduces or even prevents the occurrence of skin irritation or skin rash as well as the formation of malodor due to microbial activity. Indeed the use of these esters in the articles of the present invention, especially hygienic disposable absorbent articles, able to provide the article with the additional benefit of deodorancy effect on the skin/intimate area.

Highly preferred emollients for use herein are the alcohol, ester or acid derivatives according to the following formulae:

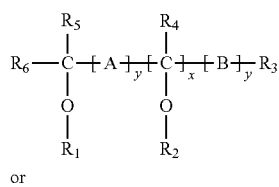

(I)

or

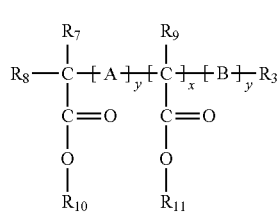

(II)

wherein $R_1$ and each $R_2$ independently are an acyl group with from 2 to 22 carbon atoms, or an alkyl, alkenyl, arylalkyl, hydroxyalkyl group with from 1 to 24 carbon atoms or hydrogen, whereby preferably at least one of $R_1$ and $R_2$ is such an acyl group; $R_3$, $R_4$, $R_5$, $R_6$, $R_7$, $R_8$, and $R_9$ are independently an alkyl, alkenyl, arylalkyl, hydroxyalkyl, alkoxy groups of from 1 to 24 carbon atoms, hydroxy group or hydrogen; $R_{10}$ and $R_{11}$ are independently an alkyl, alkenyl, arylalkyl, hydroxyalkyl, alkoxy groups of from 2 to 24 carbon atoms, hydroxy group or hydrogen; A and B are independently a $C_1$-$C_6$ linear or branched alkylene, alkyl, alkenylene, alkoxylene, alkoxyl, hydroxyalkylene, hydroxyalkyl groups; the values of x are independently from 0 to 15; the values of y are independently 0 or 1, typically with the proviso that when x=2 and y=0, at least one $R_2$ is an alkyl, alkenyl, arylalkyl, hydroxyalkyl group with from 1 to 24 carbon atoms or hydrogen.

Particular suitable alcohol derivatives for use herein are those according to formulae (I) herein above, wherein the values of x are independently from 0 to 15, y=0, $R_1$ and $R_2$ are independently hydrogen, alkyl or alkenyl group of 1 to 24 carbon atoms, with the proviso that at least $R_1$ or $R_2$ is hydrogen, $R_3$, $R_4$, $R_5$ and $R_6$ are independently an alkyl or alkenyl group of from 1 to 3 carbon atoms or hydrogen. Highly preferred alcohol derivatives are propylene glycol or polyethylene glycol.

Preferred are the ester compounds as defined above, wherein the compound is of formula (I) or (II) wherein x is 1 or 2, y is 0; $R_1$ and one $R_2$ are a $C_2$-$C_{16}$ acyl group, $R_{10}$ and one or more $R_{11}$ are a $C_2$-$C_{16}$ alkyl group; $R_3$, $R_4$, $R_5$, $R_6$, $R_7$ and $R_8$ are hydrogen, $R_9$ is independently H, or hydroxy group.

It is even more preferred that the ester derivative is a mono or diester of formula (II), most preferably a mono or diester of citric acid or tartaric acid (or salts thereof), or a triester of citric acid.

Another preferred ester derivatives for use herein is an ester compound of the formula:

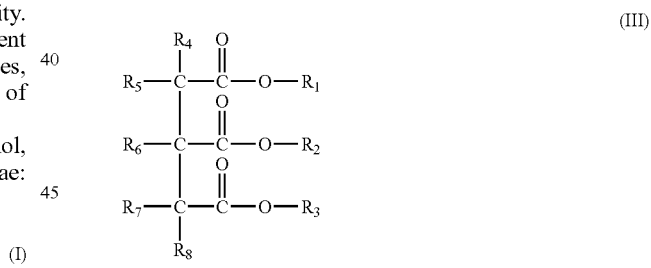

(III)

wherein $R_1$, $R_2$ and $R_3$ are independently an acyl, alkyl or alkenyl or hydroxyalkyl group with from 1 to 22 carbon atoms, and $R_4$, $R_5$, $R_6$, $R_7$ and $R_8$ are independently selected from the group consisting of $C_1$-$C_{10}$ linear or branched alkyl, acyl, alkenyl, hydroxyalkyl or alkoxy groups, hydroxy, chloride, bromide, amine or hydrogen.

Highly preferred are the compounds above wherein $R_4$, $R_5$, $R_7$ and $R_8$ of said compound are hydrogen, R6 is hydrogen, hydroxy, C1-C4 linear or branched alkyl, alkenyl, hydroxyalkyl or alkoxy groups and preferably wherein $R_1$, $R_2$ and $R_3$ are independently an C1-C4 alkyl group or hydrogen.

Such preferred ester derivatives include triethyl citrate, acetyl tributhyl citrate, triacetyl citrate, O acetyl triethyl citrate. Highly preferred is triethyl citrate. Triethyl citrate is commercially available from Aldrich.

Optional Agents

The articles according to the present invention may further comprise other conventional agents or mixtures thereof.

Optional Odour Control Agents

Odour control agent or combinations thereof, known in the art for this purpose may be used herein. These agents can typically be classified according to the type of odour the agent is intended to combat. Odors may be chemically classified as being acidic, basic or neutral.

Alternatively, the odor control agents may be categorized with respect to the mechanism by which the malodor detection is reduced or prevented. For example, odor control agents which chemically react with malodorous compounds or with compounds which produce malodorous degradation products thereby generating compounds lacking odor or having an odor acceptable to consumers may also be utilized herein.

Suitable odor control agents for use herein typically include carboxylic acids such as citric acid, lauric acid, boric acid, adipic acid and maleic acid, oxidizing agents, antimicrobial agents, activated carbons, clays, zeolites, silicates, silica, diatomaceous earth and starches. Such odor control agents and systems are disclosed in more details in EP-A-348 978, EP-A-510 619, WO 91/12029, WO 91/11977, WO 91/12030, WO 81/01643 and WO 96/06589, which are all incorporated herein by reference. Highly preferred odor control agents are zeolite together with silicate and/or silica.

In a preferred embodiment herein the article, especially hygienic absorbent article, further comprises, as the odor control agents, zeolite together with silicate/silica in a weight ratio of silicate/silica to zeolite of from 1.5 to 5.1, preferably from 3.1 to 1.3 and most preferably about 1.1. This combination has been found to be particularly effective in terms of odor control over a broad range of malodorous compounds. Silicate/silica and zeolite have a complementary odor control properties towards various malodorous compounds, thereby resulting in outstanding overall odor control reduction.

Alternative odor control agents are ion exchange resins such as those described in U.S. Pat. No. 4,289,513 and U.S. Pat. No. 3,340,875.

Suitable odor control agents also include chelating agents and may be selected from amino carboxylates such as for example ethylenediamine-tetracetate, as described for example in U.S. Pat. No. 4,356,190, amino phosphonates such as ethylenediaminetetrakis (methylene-phosphonates), polyfunctionally-substituted aromatic chelating agents as described in U.S. Pat. No. 3,812,044 and mixtures thereof. Without intending to be bound by theory it is believed that the benefit of these materials is in part due to their exceptional ability to remove iron, copper, calcium, magnesium and manganese ions present in the absorbed fluids and their degradation products by the formation of chelates.

Another suitable odor control agent for use herein is an acidic pH buffer system, such as citric acid and sodium bicarbonate, sodium phosphate and sorbic acid buffer systems.

Typically, the articles herein may comprise the odor control agent or a mixture thereof at a level of from 0 $gm^{-2}$ to 600 $gm^{-2}$, preferably from 5 to 500 $gm^{-2}$, more preferably from 10 $gm^{-2}$ to 350 $gm^{-2}$ and most preferably from 20 $gm^{-2}$ to 200 $gm^{-2}$ In one aspect of the invention the articles according to the present invention might also comprise on top of the cooling agents, any perfumes or mixtures thereof. Such articles might be particularly beneficial for further improving pleasantness to wearer. Indeed, without to be bound by theory the presence of selected perfume is believed to increase freshness perception, and cleanness feeling. Also the presence of perfumes controls malodor emanating typically from body fluids, by their odor masking activity. In another aspect of the invention, the articles according to the present invention are free of any perfumes. The addition of perfume might not be desirable by some wearer of hygienic feminine protection articles who might associate their presence to the presence of odor perceived as a negative in intimate feminine care and/or as causing potential skin irritation.

Incorporation of the Cooling Agent into the Articles

Vehicle

The cooling agent for use in the article of the invention may be water-soluble or lipid-soluble and may be incorporated into the article neat, such as in dry powder or particulate form, or in the form of a solution, suspension, dispersion, emulsion or the like in a dermatologically acceptable carrier vehicle that does not interfere with the freshness effect of cooling agent. The cooling agent may also be incorporated in another structure that in turn is incorporated into the article during manufacture or assembly. For example, the cooling agent may be coated onto or otherwise attached or bound to a nanophase particulate structure or other solid support such as glass, plastic or agarose beads, and the like, or contained in pressure-rupturable or dissolvable microcapsules and the like, or contained in an absorbent material. The use of other types of incorporable elements for containing the cooling agent and methods for their incorporation will be readily apparent to one skilled in the art.

Carrier vehicles for the cooling agent include compositions that are in the form of lotions, creams, oils, ointments, powders, foams, or gels and the like and that may contain any ingredients commonly used in the art for such compositions. The ingredients of the compositions will depend on the character of the composition; thus, for example, lotions will generally comprise different ingredients than powders. It is preferable that cooling agent-containing compositions intended for transfer to the skin have a pH of no less than about 4 and no greater than about 7.5.

Incorporation

The cooling agent employed in the articles of the invention is incorporated into the article in a configuration that does not itself interfere with the normal function of the various structures of the article (e.g., the absorbency of the core, the liquid perviousness of the topsheet, and the like for hygienic absorbent articles). The cooling agent may be incorporated into any portion or portions of the article including, but not limited to, the topsheet, the backsheet, the absorbent core, any secondary layer(s) intermediate the core and sheet layers, a leg cuff, a side panel, a waist region, wings, a fastener, an insertable element such as an absorbent material inserted into the absorbent article for use during wear of the article, specialized structures such as those employed to contain bowel movements (e.g., bowel movement "pockets"), and the like. The cooling agent may be incorporated into the article neat or, alternatively, the cooling agent may be contained in a delivery system described herein before that is incorporated into any of the foregoing portions of the article and that delivers the cooling agent directly or indirectly to the skin of a wearer during normal wear of the article.

Any number of different cooling agent or mixtures of cooling agents, whether or not they are incorporated into a delivery system, may be uniformly or nonuniformly distributed throughout the article and/or onto the surface of one layer or several layers of the article.

Preferably the cooling agent may be incorporated directly onto the surface (typically wearer-facing surface) of or within the structure of any type of topsheet, including woven, nonwoven and apertured structured topsheets, the backsheet, and/or absorbent core materials, or other components of the article during manufacture or assembly by diverse methods which will be readily apparent to those skilled in the art. For example the cooling agent can be applied, optionally after being dispersed in a liquid or semi-solid carrier vehicle, to the topsheet, to the absorbent core, or to the core side of the backsheet, by spraying, dipping, printing, soaking or otherwise contacting the selected structural element with the cooling agent and optionally its carrier vehicle. Among the many other techniques that can be employed are graft or radical polymerization, or steam treating of the structural elements in order to bind the cooling agent by hydrogen bonding that is easily reversed when such surfaces are wetted by body waste to release the cooling agent.

Preferably, the cooling agent is incorporated into at least a portion of a wearer-facing surface of the article and is available for automatic transfer to the wearer's skin and/or mucosal surface during normal contact, wearer motion and/or body heat during wear of the article. Alternatively, the article further comprises a delivery system that contains the cooling agent and, during wear of the article the delivery system automatically delivers at least a portion of the cooling agent to the skin and/or mucosal surface of the wearer. In a more preferred embodiment, the delivery system is an emollient-containing composition containing the cooling agent and various emollients, as described hereinbefore, that is delivered directly from a wearer-facing surface to the wearer's skin to perform an immediate and sustained freshness sensation while maintaining or even improving skin health.

The Article

The articles according to the present invention, including hygienic disposable articles (e.g., diapers, adult incontinence products, underarm sweat products, collar inserts, sanitary napkins, pantiliners and the like) are typically provided in color communicating a hygienic condition. This conventionally results in white or predominantly white articles. This did fit well with the historically predominant undergarment color in which these articles are worn, namely white undergarments. With recent trend in fashion the tendency is to wear undergarments of colors matching the colors of the cloths, including black, purple, red, yellow, green and the like. Actually any color is suitable for the articles to be worn in contact with body, including primary colors and combinations thereof in any tonality. Advantageously by providing the articles, especially hygienic articles in colors matching the colors of the undergarments, enhanced discretion in use is obtained. The article might be colored only on the wearer facing surface and/or on the garment facing surface or might be colored through its thickness. The colored might be uniform or non-uniform, multicolor image might also be used depending on end used of the articles.

Furthermore it has been found that by selecting specific colors, the choice of such colors further contributes to the freshness sensation delivered by present articles and hence participates to cleanness and comfort feeling. Particular preferred colors are green and/or blue which are believed to stimulate relaxing and freshness sensation. The choice of color might be triggered by the emotion/mood that is desired during wearing experience, this influence of the color on mood is known from chromo-therapy and might be selected as appropriate.

The article typically comprises a substrate made of a nonwoven material, or a woven material or a polymeric film, or a gel. Such films and nonwovens or wovens materials can be made for example from polymers such as polyethylene or polypropylene compositions. Conventionally such polymers have been provided with a coloring material such as titanium dioxide to provide a white opacity. Simply using other coloring materials (e.g., dyes, pigments and so on) namely coloring materials like black, navy bleu, green, yellow, gray and the like, provides a colored film or material of other color than white.

It is to be understood herein that any conventional method known to those skilled in the art to provide colored substrates is suitable for use herein. Colored substrates can typically be provided by different methods well known to those skilled in the art, including pigmenting the materials, dying the materials or color printing the materials.

The articles according to the present invention are preferably breathable and typically have a water vapour permeability (as measured by the water vapour permeability test method described herein after) higher than 100 $(g)/(m^2/24\ hrs)$, preferably of more than 200 $(g)/(m^2/24\ hrs)$, more preferably higher than 300 $(g)/(m^2/24\ hrs)$, and most preferably higher than 400 $(g)/(m^2/24\ hrs)$.

Particularly preferred articles according to the present invention are hygienic disposable absorbent articles as those described as follows:

They typically comprise a topsheet directly facing the wearer in use, and a backsheet directly facing the garment in use, and an absorbent core sandwiched there between Absorbent Core According to the present invention, the absorbent core can include the following components: (a) an optional primary fluid distribution layer preferably together with a secondary optional fluid distribution layer; (b) a fluid storage layer; (c) an optional fibrous ("dusting") layer underlying the storage layer; and (d) other optional components. According to the present invention the absorbent may have any thickness depending on the end use envisioned.

a Primary/Secondary Fluid Distribution Layer

One optional component of the absorbent according to the present invention is a primary fluid distribution layer and a secondary fluid distribution layer. The primary distribution layer typically underlies the topsheet and is in fluid communication therewith. The topsheet transfers the acquired fluid to this primary distribution layer for ultimate distribution to the storage layer. This transfer of fluid through the primary distribution layer occurs not only in the thickness, but also along the length and width directions of the absorbent product. The also optional but preferred secondary distribution layer typically underlies the primary distribution layer and is in fluid communication therewith. The purpose of this secondary distribution layer is to readily acquire fluid from the primary distribution layer and transfer it rapidly to the underlying storage layer. This helps the fluid capacity of the underlying storage layer to be fully utilized. The fluid distribution layers can be comprised of any material typical for such distribution layers. In particular fibrous layers maintain the capillaries between fibers even when wet are useful as distribution layers.

b Fluid Storage Layer

Positioned in fluid communication with, and typically underlying the primary or secondary distribution layers, is a fluid storage layer. The fluid storage layer typically comprises any usual absorbent gelling material. It preferably comprises such materials in combination with suitable carriers.

Suitable carriers include materials, which are conventionally utilized in absorbent structures such as natural, modified or synthetic fibers, particularly modified or non-modified cellulose fibers, in the form of fluff and/or tissues. Most preferred are tissue or tissue laminates in the context of sanitary napkins and panty liners.

An embodiment of the absorbent structure made according to the present invention may comprise multiple layers comprises a double layer tissue laminate typically formed by folding the tissue onto itself. These layers can be joined to each other for example by adhesive or by mechanical interlocking or by hydrogen bridge bands. Absorbent gelling materials and/or other optional materials can be comprised between the layers.

Modified cellulose fibers such as the stiffened cellulose fibers can also be used. Synthetic fibers can also be used and include those made of cellulose acetate, polyvinyl fluoride, polyvinylidene chloride, acrylics (such as Orlon), polyvinyl acetate, non-soluble polyvinyl alcohol, polyethylene, polypropylene, polyamides (such as nylon), polyesters, bicomponent fibers, tricomponent fibers, mixtures thereof and the like. Preferably, the fiber surfaces are hydrophilic or are treated to be hydrophilic. The storage layer can also include filler materials, such as Perlite, diatomaceous earth, Vermiculite, etc., to improve liquid retention.

If the absorbent gelling materials are dispersed non-homogeneously in a carrier, the storage layer can nevertheless be locally homogenous, i.e. have a distribution gradient in one or several directions within the dimensions of the storage layer. Non-homogeneous distribution can also refer to laminates of carriers enclosing absorbent gelling materials partially or fully.

c Optional Fibrous ("Dusting") Layer

An optional component for inclusion in the absorbent core according to the present invention is a fibrous layer adjacent to, and typically underlying the storage layer. This underlying fibrous layer is typically referred to as a "dusting" layer since it provides a substrate on which to deposit absorbent gelling material in the storage layer during manufacture of the absorbent core. Indeed, in those instances where the absorbent gelling material is in the form of macro structures such as fibers, sheets or strips, this fibrous "dusting" layer need not be included. However, this "dusting" layer provides some additional fluid-handling capabilities such as rapid wicking of fluid along the length of the pad.

d Other Optional Components of the Absorbent Structure

The absorbent core according to the present invention can include other optional components normally present in absorbent webs. For example, a reinforcing scrim can be positioned within the respective layers, or between the respective layers, of the absorbent core. Such reinforcing scrims should be of such configuration as to not form interfacial barriers to fluid transfer. Given the structural integrity that usually occurs as a result of thermal bonding, reinforcing scrims are usually not required for thermally bonded absorbent structures.

The Topsheet

According to the present invention the absorbent article comprises as an essential component a topsheet. The topsheet may comprise a single layer or a multiplicity of layers. In a preferred embodiment the topsheet comprises a first layer which provides the user facing surface of the topsheet and a second layer (also called secondary topsheet) between the first layer and the absorbent structure/core.

The topsheet as a whole and hence each layer individually needs to be compliant, soft feeling, and non-irritating to the wearer's skin. It also can have elastic characteristics allowing it to be stretched in one or two directions. According to the present invention the topsheet may be formed from any of the materials available for this purpose and known in the art, such as woven and non woven fabrics and films. In a preferred embodiment of the present invention at least one of the layers, preferably the upper layer, of the topsheet comprises a hydrophobic, liquid permeable apertured polymeric film. Preferably, the upper layer is provided by a film material having apertures which are provided to facilitate liquid transport from the wearer facing surface towards the absorbent structure. If present the lower layer preferably comprises a non woven layer, an apertured formed film or an airlaid tissue.

The Backsheet

The backsheet primarily prevents the extrudes absorbed and contained in the absorbent structure from wetting articles that contact the absorbent product such as underpants, pants, pyjamas and undergarments. The backsheet is preferably impervious to liquids (e.g. menses and/or urine) and is preferably manufactured from a thin plastic film, although other flexible liquid impervious materials can also be used. As used herein, the term "flexible" refers to materials that are compliant and will readily conform to the general shape and contours of the human body. The backsheet also can have elastic characteristics allowing it to stretch in one or two directions. In a preferred embodiment the backsheet comprises a first layer which provides the garment facing surface of the backsheet and a second layer (also called secondary backsheet) between the first layer and the absorbent structure/core.

The backsheet typically extends across the whole of the absorbent structure and can extend into and form part of or all of the preferred sideflaps, side wrapping elements or wings.

In addition to the prevention of liquid transport through the backsheet, the backsheet is preferably breathable. Hence the backsheet also permits the transfer of water vapour and preferably both water vapour and air through it and thus allows reduction of humid and occlusive environment on the skin contacted with the article. Breathable is preferred herein as it contributes to further improve the freshness sensation and dry feeling associated with the present invention. Even more preferred herein the disposable absorbent articles have both a breathable backsheet and an apertured polymeric film topsheet for further improved freshness sensation of the articles.

Suitable breathable backsheets for use herein include all breathable backsheets known in the art. In principle there are two types of breathable backsheets, single layer breathable backsheets which are breathable and impervious to liquids and backsheets having at least two layers, which in combination provide both breathability and liquid imperviousness.

Suitable single layer breathable backsheets for use herein include those described for example in GB A 2184 389, GB A 2184 390, GB A 2184 391, U.S. Pat. No. 4,591,523, U.S. Pat. No. 3,989,867, U.S. Pat. No. 3,156,242 and WO 97/24097.

Suitable dual or multi layer breathable backsheets for use herein include those exemplified in U.S. Pat. No. 3,881,489, U.S. Pat. No. 4,341,216, U.S. Pat. No. 4,713,068, U.S. Pat. No. 4,818,600, EP 203 821, EP 710 471, EP 710 472, WO 97/24095, WO 97/24096, WO 97/24097 and EP 793 952.

Particularly preferred are backsheets meeting the requirements as defined in European Patent Application EP813849 and more preferably wherein the absorbent article also meets the requirements as described therein.

The breathable backsheet may comprise at least one, preferably at least two water vapour permeable layers. Suitable water vapour permeable layers include 2-dimensional, planar micro and macro-porous films, monolithic films, macroscopically expanded films and formed apertured films. According to the present invention the apertures in said layer may be of any configuration, but are preferably spherical or oblong. The apertures may also be of varying dimensions. In a preferred embodiment the apertures are preferably evenly distributed across the entire surface of the layer, however layers having only certain regions of the surface having apertures is also envisioned.

2-dimensional planar films as used herein have apertures having an average diameter of from 1 micrometers to 200 micrometers. Typically, 2-dimensional planar micro porous films suitable for use herein have apertures having average diameters of from 150 micrometers to 1 micrometers, preferably from 120 micrometers to 10 micrometers, most preferably from 90 micrometers to 15 micrometers. Typical 2-dimensional planar macroporous films have apertures having average diameters of from 200 micrometers to 90 micrometers. Macroscopically expanded films and formed apertured films suitable for use herein typically have apertures having diameters from 100 micrometers to 500 micrometers. Embodiments according to the present invention wherein the backsheet comprises a macroscopically expanded film or an apertured formed film, the backsheet will typically have an open area of more than 5%, preferably from 10% to 35% of the total backsheet surface area.

Suitable 2-dimensional planar layers of the backsheet may be made of any material known in the art, but are preferably manufactured from commonly available polymeric materials. Suitable materials are for example GORE-TEX™ or Sympatex™ type materials well known in the art for their application in so-called breathable clothing. Other suitable materials include XMP-1001 of Minnesota Mining and Manufacturing Company, St. Paul, Minn., USA. As used herein the term 2-dimensional planar layer refers to layers having a depth of less than 1 mm, preferably less than 0.5 mm, wherein the apertures have an average uniform diameter along their length and which do not protrude out of the plane of the layer. The apertured materials for use as a backsheet in the present invention may be produced using any of the methods known in the art such as described in EP 293 482 and the references therein. In addition, the dimensions of the apertures produced by this method may be increased by applying a force across the plane of the backsheet layer (i.e. stretching the layer).

Suitable apertured formed films include films which have discrete apertures which extend beyond the horizontal plane of the garment facing surface of the layer towards the core thereby forming protuberances. The protuberances have an orifice located at their terminating ends. Preferably said protuberances are of a funnel shape, similar to those described in U.S. Pat. No. 3,929,135. The apertures located within the plane and the orifices located at the terminating end of protuberance themselves maybe circular or non circular, provided the cross sectional dimension or area of the orifice at the termination of the protuberance is smaller than the cross sectional dimension or area of the aperture located within the garment facing surface of the layer.

Preferably said apertured preformed films are uni directional such that they have at least substantially, if not complete one directional fluid transport towards the core. Suitable macroscopically expanded films for use herein include films as described in for example in U.S. Pat. No. 637,819 and U.S. Pat. No. 4,591,523.

Suitable macroscopically expanded films for use herein include films as described in for example U.S. Pat. No. 4,637, 819 and U.S. Pat. No. 4,591,523.

Suitable monolithic films include Hytrel™, available from DuPont Corporation, USA, and other such materials as described in Index 93 Congress, Session 7A "Adding value to Nonwovens", J-C. Cardinal and Y. Trouilhet, DuPont de Nemours International S.A., Switzerland.

The backsheet may comprise in addition to said water vapour permeable layer additional backsheet layers. Said additional layers may be located on either side of said water vapour permeable layer of the backsheet. The additional layers may be of any material, such as fibrous layers or additional water vapour permeable layers as described herein above.

In a particularly preferred embodiment herein a dual or multiple layer breathable backsheet composite is used in the absorbent article. Suitable breathable backsheets for use herein comprise at least a first and a second layer. The first layer is positioned between the garment facing surface of the absorbent core and the wearer facing surface of the second layer. It is oriented such that it retards or prevents liquid from passing from the absorbent core towards the outside while allowing free air flow and water vapor through it. The second layer provides water vapor and air permeability so as to support breathability of the article. In addition to water vapor permeability the air permeability is desirable in order to further improve the comfort benefit from the breathability of the article.

Such a first layer is preferably in direct contact with the absorbent core. It provides air and water vapor permeability by being apertured. Preferably this layer is made in accordance with the aforementioned U.S. Pat. No. 5,591,510 or PCT WO 97/03818, WO 97/03795. In particular, this layer comprises a polymeric film having capillaries. The capillaries extend away from the wearer facing surface of film at an angle which is less then 90 degrees. Preferably the capillaries are evenly distributed across the entire surface of the layer, and are all identical. However, layers having only certain regions of the surface provided with apertures, for example only an area outside the region aligned with the central loading zone of the absorbent core, maybe provided with such capillaries.

Methods for making such three-dimensional polymeric films with capillary apertures are identical or similar to those found in the apertured film topsheet references, the apertured formed film references and the micro-/macroscopically expended film references cited above. Typically a polymeric film such as a polyethylene (LDPE, LLDPE, MDPE, HDPE or laminates thereof) or preferably a monolithic polymeric film is heated close to its melting point and exposed through a forming screen to a suction force which pulls those areas exposed to the force into the forming apertures which are shaped such that the film is formed into that shape and, when the suction force is high enough, the film breaks at its end thereby forming an aperture through the film.

Especially using a monolithic polymer film as the material for the first layer provides water vapor permeability even under stress conditions. While the apertures provide air permeability during "leakage safe" situations but close the capillaries under stress conditions the monolithic material maintains water vapor permeability in such a case. Preferred breathable monolithic film materials for use herein are those having a high vapor exchange. Suitable monolithic films include Hytrel™, available from DuPont Corporation, USA, and other such materials as described in Index 93 Congress, Session 7A "Adding value to Nonwovens", J-C. Cardinal and Y. Trouilhet, DuPont de Nemours international S.A, Switzerland.

Various forms, shapes, sizes and configurations of the capillaries are disclosed in EP-A-934 735 and EP-A-934 736 both of which are herein incorporated for reference. In particular the apertures form capillaries, which have side walls. The capillaries extend away from the wearer facing surface of the film for a length which typically should be at least in the order of magnitude of the largest diameter of the aperture while this distance can reach up to several times the largest aperture diameter. The capillaries have a first opening in the plane of the garment facing surface of the film and a second opening which is the opening formed when the suction force (such as a vacuum) in the above mentioned process creates the aperture. Naturally the edge of the second opening may be rugged or uneven, comprising loose elements extending from the edge of the opening. However, it is preferred that the opening be as smooth as possible so as not to create a liquid transport entanglement between the extending elements at the end of the second opening of the capillary with the absorbent core in the absorbent article (in contrast this may be desirable for apertured film topsheets where such loose elements provide the function of sucker feet). The capillaries in the first layer of the breathable backsheet allow air and water vapor permeability which is not hindered by them being slanted at an angle or by the shape. At the same time the slanting and shaping will allow the capillaries to close under pressure excerpted from the wearer facing side on them such that liquid transport through the capillaries towards the outside of the article becomes nearly impossible. Hence these three-dimensional formed film layers are highly preferable in the context of breathable absorbent articles and in particular so with the additional second outer layer which is provided as hereinafter explained.

The second outer layer of the breathable backsheet according to the present invention is a fibrous nonwoven web having a basis weight of less than 40 g/m2, preferably of less than 28 g/m2. More preferably, the second outer layer is a fibrous nonwoven web formed by a layered composite of a meltblown nonwoven layer made from synthetic fibers having a basis weight of less than 13 g/m2 and of a spunbonded nonwoven layer also made from synthetic fibers.

In the most preferred embodiment herein the backsheet comprises at least a first layer of a resilient, three dimensional web which consists of a liquid impervious polymeric film having apertures forming capillaries which are not perpendicular to the plane of the film but are disposed at an angle of less than 90° relative to the plane of the film, and at least a second breathable layer of a porous web which is a fibrous nonwoven composite web of a meltblown nonwoven layer made from synthetic fibers having a basis weight of less than 13 g/m2 and of a spunbonded nonwoven layer made from synthetic fibers.

Using as the breathable backsheet in the absorbent article of the present invention, a backsheet comprising at least one breathable layer of a resilient, three dimensional web which consists of a liquid impervious polymeric film having apertures forming capillaries which are not perpendicular to the plane of the film but are disposed at an angle of less than 90° relative to the plane of the film, and at least another breathable layer of a porous web which consists of a fibrous nonwoven web having a basis weight of less than 40 g/m2 (particularly of about 28 g/m2), further contributes to the outstanding benefit of the present invention. Indeed these backsheet functions very well in term of comfort, soiling prevention of the user panty, dryness, etc. while providing additional comfort due to the reduced basis weight of the non-woven layer.

This reduction of basis weight also provides an improved material consumption structure of the whole article.

According to the present invention the absorbent article may find utility as sanitary napkins, panty liners, adult incontinence products, nursing pads and baby diapers. The present invention finds particular susceptibility as sanitary napkins and panty liners. Thus in addition to the components described herein above, the absorbent article may also comprise all those features and parts which are typical for products in the context of their intended use such as wings and side flaps, undergarment adhesive means, release paper, wrapping elements, fastening means and the like.

Moisture Vapour Permeability Test

The basic principle of the test is to quantify the extent of water vapour transmission of a backsheet construction and/or an article. The test method that is applied is based on a standardized textile industry applied test method and commonly referred to as the "cup test method". The test is performed in a stable temperature/humidity laboratory maintained at a temperature of 23° C. at 50% RH for a period of 24 hours.

Apparatus

1) Sample cup of open area=0.00059 m$^2$
2) Syringe to introduce the distilled water into the completed sample cup.
3) Wax to seal the cup once sample has been arranged.
4) A circular punch to facilitate preparation circular samples of diameter=30 mm.
5) Laboratory of stable climatic conditions (23° C.±0.5° C./50% RH±1% RH)
6) Laboratory balance accurate to 4 decimal places.

Sample Preparation/Measurements

The test is to be performed on the article or the backsheet construction. A representative article or backsheet is selected and a sample is cut to size using the punch. The sample cut is sufficiently large to adequately overlap the sample holder and to ensure material that may have been damaged or undesirably stretched due to the cutting operation lies outside of the measurement centre when the measurement is performed. The sample is so arranged onto of the sample cup so as to fully overlap the cup. The sample is oriented so as to ensure that the surface exposed to the laboratory environment is the same that would be found while wearing the article.

The closure ring of the sample cup is then placed onto the sample and pushed down. This ensures that the excess material is held firmly in place and does not interfere with the measurement. A wax is then applied to the entire surface of the closure ring to ensure the whole upper part of the apparatus is closed to the environment. Distilled water (5±0.25 ml) is introduced with the syringe into the sealed sample cup via the minute perforation. Finally this perforation is sealed with silicone grease.

The entire cup (containing sample and water) is weighed and the weight recorded to 4 decimal places. The cup is then placed in a ventilation stream generated by a fan. The air flowing over the top of the sample cup is 3±0.3 m/sec and confirmed via a wind velocity meter ("Anemo", supplied by Deuta SpA., Italy). The sample cup remains in the ventilated test field for a period of 24 hrs and is then re-weighted. During this period if the test sample is sufficiently breathable the liquid in the sample holder is able to diffuse out of the sample holder and into the laboratory environment. This results in a reduction in the weight of water in the sample holder that can be quantified on re-weighing the complete sample cup following the 24 hr period. The vapour permeability value is determined as the weight loss divided by the open area of the sample holder and quoted per day.

i.e. Vapour Permeability=Weight Loss (g)/(0.00059 m$^2$/24 hrs.)

The present invention is further illustrated by the following examples

EXAMPLES

Example 1

Panty liners were prepared by modifying panty liners commercially available, namely "Alldays"® manufactured by Procter & Gamble, Germany.

The topsheet is a film/non woven composite {film supplier code 45105 BP Chemical Plastic Germany, non woven supplier code T-27 AXC Corolind HDPE LINOTEC)

30 g/m$^2$ of an emollient-containing composition consisting of 23% by weight of menthyl lactate available from H&R (Germany) under the name Frescolat ML® and of 77% by weight of triethyl citrate (available from Aldrich) was sprayed homogenously over the whole surface of the wearer-facing surface of the topsheet.

The core is an airlaid material containing an absorbing gelling compound having a basis weight of 100 g/m$^2$ and available from Concert under the code GH 100.91209.

The backsheet comprises two layers a first layer and a second layer. The first layer (also called secondary backsheet) is in contact with the absorbent tissue and the second layer. The second layer is in contact with the first layer and the undergarment of the wearer. The first layer is a formed apertured film (HEX) {supplied by Tredegar Film Products B. V. Holland under the manufacturing code X-25368}. The second layer is composed of a microporous layer {supplied by EXXON Company IL under the manufacturing code EXXAIRE BF112 W}. Each backsheet layer is joined over the full surface by an extensively overlapped spiral glue application at a basis weight of approximately 8 g/m$^2$. The glue used for attachment of both backsheet layers was supplied by SAVARE' SpA. Italy (under the material code PM17).

Example 2

This panty liner is based on a 'Alldays'® panty liner available from Procter & Gamble Germany, which has been modified.

The topsheet is a film/non woven composite {film supplier code 45105 BP Chemical Plastic Germany, non woven supplier code T-27 AXC Corolind HDPE LINOTEC)

30 g/m$^2$ of an emollient-containing composition consisting of 23% by weight of menthyl lactate available from H&R (Germany) under the name Frescolat ML® and of 77% by weight of triehyl citrate (available from Aldrich) was sprayed homogenously over the whole surface of the wearer-facing surface of the topsheet.

The core material is a tissue laminate (13.2 cm×4.0 cm) composed of a 2 layers of airlayed tissue of 55 g/m$^2$ basis weight {available from Unikay Italy under the supplier code Unikay 303 LF}. Between the two tissue layers the laminate contains an absorbing gelling material, namely Agm Aqualic (available from Shokubai under the code Aqualic L-74) and an odor control material namely Zeolite A (available from Degussa under the code Zeolite Wessalith CS).

The backsheet comprises two layers a first layer and a second layer. The first layer (also called secondary backsheet) is in contact with the absorbent tissue and the second layer. The second layer is in contact with the first layer and the undergarment of the wearer. The first layer is a formed apertured film (HEX) {supplied by Tredegar Film Products B.V. Holland under the manufacturing code X-25368}. The second layer is composed of a microporous layer {supplied by EXXON Company IL under the manufacturing code EXXAIRE BF112 W}. Each backsheet layer is joined over the full surface by an extensively overlapped spiral glue application at a basis weight of approximately 8 g/m$^2$. The glue used for attachment of both backsheet layers was supplied by SAVARE' SpA. Italy (under the material code PM 17).

Example 3

These are examples of sanitary napkins according to the present invention. The sanitary napkins are based on an 'Always Ultra'® sanitary napkin available from Procter & Gamble Germany, which has been modified.

The topsheet is a film/airlaid composite, with a first outer topsheet layer made of an apertured film (S-RIS CPM material available from Tredegar Holland under the code X-25602) and a second topsheet layer, positioned between the first outer topsheet layer and the core, made of air laid material (available from DUNI Sweden under the code PTC X 077).

30 g/m$^2$ of an emollient-containing composition consisting of 23% by weight of menthyl lactate available from H&R (Germany) under the name Frescolat ML® and of 77% by weight of triehyl citrate (available from Aldrich) was sprayed homogenously over the whole surface of the wearer-facing surface of the topsheet, i.e. the outer surface of the apertured film. Alternatively only the wearer-facing surface of the air-laid second topsheet layer was homogeneously sprayed with the emollient-containing composition or both the airlaid second topsheet layer and the first apertured topsheet layer.

The core material is an airlaid core containing Agm available from Concert (Germany) under the name GH 150 1006.

The backsheet is a multi-layer breathable backsheet comprising a formed apertured film backsheet layer and a second microporous layer. The first layer is a PE film with a crush resistant hexagonal hole configuration {supplied by Tredegar Film Products B.V. Holland under the manufacturing code X 25368). The second layer of backsheet has been replaced by a microporous layer (manufactured by Tredegar Hungary under the name XBF 610W)

Further Examples

Additional pantiliners as the ones of Examples 1 or 2 as well as additional sanitary napkins as the ones of Example 3 above were prepared, except that instead of spraying the emollient-containing composition mentioned in the examples 1 to 3 above, the following compositions were sprayed homogenously over the whole surface of the wearer-facing surface of the topsheet:
Either
    30 g/m$^2$ of an emollient-containing composition consisting of 20% by weight of menthoxypropanediol available from Takasago under the name TK-10® and of 80% by weight of triethyl citrate or triacetyl citrate (available from Aldrich).
or
    20 g/m$^2$ of an emollient-containing composition consisting of 20% by weight of menthone glycerol ketal available from H&R under the name Frescolat MGA® and of 80% by weight of triethyl citrate or triacetyl citrate (available from Aldrich).
or
    20 g/m$^2$ of an emollient-containing composition consisting of 20% by weight of ethyl menthane carboxamide available from Givaudan Roure under the name WS3® and of 80% by weight of triethyl citrate or triacetyl citrate (available from Aldrich).
or
    30 g/m$^2$ of an emollient-containing composition consisting of 30% by weight of ethyl menthane carboxamide available from Givaudan Roure under the name WS3® and of 70% by weight of propylene glycol (available from Aldrich).
or
    40 g/m$^2$ of an emollient-containing composition consisting of 30% by weight of menthyl lactate available from Haarman&Reimer (Germany) under the name Frescolat®ML and of 70% by weight of propylene glycol (available from Aldrich).

All sanitary napkins and panty-liners illustrated herein before were found to improve comfort to the wearer in use, including providing a quasi immediate freshness sensation (after only about 2 minutes of wearing time) and long lasting freshness sensation (over more than 3 to 4 hours), while maintaining or even improving skin health.

Example A

An example of other article to be worn in contact with body is a shoe insole particularly suitable to be used in shoes in direct contact with feet in absence of socks (e.g., in summer time). The shoe insole is made of an air laid tissue of 55 g/m² basis weight {available from Unikay Italy under the supplier code Unikay 303 LF} on which one surface (the one intended to directly face the foot of the user) has been homogeneously sprayed with 0.5 g/m² of an emollient-containing composition consisting of 23% by weight of menthyl lactate available from H&R (Germany) under the name Frescolat ML® and of 77% by weight of triehyl citrate (available from Aldrich).

All documents cited in the Detailed Description of the Invention are, in relevant part, incorporated herein by reference; the citation of any document is not to be construed as an admission that it is prior art with respect to the present invention.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An article suitable to be worn in contact with a mammal body, the article comprising a topsheet and a backsheet, said topsheet comprising a mint-odor free cooling agent able to convey a freshness sensation to the wearer of the article, without the need of modifying body surface temperature, wherein the cooling agent is menthone glycerol ketal;

wherein the article further comprises a delivery system for containing and delivering the cooling agent to at least a portion of the skin and/or mucosal surface of mammal wearing the article;

wherein the delivery system is an emollient-containing composition consisting essentially of from about 0.1% to about 99.9%, by weight of the emollient-containing composition of the cooling agent and from about 99.9% to about 0.1%, by weight of the emollient-containing composition of an emollient that is triethyl citrate;

wherein said article is a feminine napkin; and wherein said backsheet is an apertured polymeric film.

2. The article according to claim 1, which comprises on at least a portion of the article from about 0.01 $gm^{-2}$ to about 300 $gm^{-2}$ of a cooling agent or a mixture thereof.

3. The article according to claim 1, wherein the article comprises a wearer-facing surface wherein at least a portion of the wearer-facing surface comprises the cooling agent.

4. The article according to claim 1, wherein the article is breathable, typically has a water vapour breathability of higher than about 10 $(g)/(m^2/24\ hrs)$.

5. The article according to claim 1, wherein said article is a hygienic absorbent article comprising a topsheet as a wearer-facing surface, a backsheet as a garment-facing surface and an absorbent core sandwiched between the topsheet and backsheet, said backsheet preferably being a breathable backsheet.

6. The absorbent article according to claim 1 wherein said apertures have an average diameter of from 100 micrometers to 500 micrometers.

7. The absorbent article according to claim 1, wherein said breathable backsheet comprises at least two layers, a first layer comprising an apertured layer and a second layer comprising a fibrous layer.

8. The absorbent article according to claim 7, wherein said breathable backsheet comprises at least a first layer of a resilient, three dimensional web which consists of a liquid impervious polymeric film having apertures forming capillaries which are not perpendicular to the plane of the film but are disposed at an angle of less than 90° relative to the plane of the film, and at least a second breathable layer being a fibrous nonwoven web made from synthetic fibers having a basis weight of less than about 40 g/m2.

* * * * *